US010674924B2

(12) United States Patent
Jeong et al.

(10) Patent No.: US 10,674,924 B2
(45) Date of Patent: Jun. 9, 2020

(54) MAPPING CAVERNOUS NERVES DURING SURGERY

(71) Applicants: Chang Wook Jeong, Seoul (KR); Keewon Kim, San Francisco, CA (US)

(72) Inventors: Chang Wook Jeong, Seoul (KR); Keewon Kim, San Francisco, CA (US)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 191 days.

(21) Appl. No.: 15/901,890

(22) Filed: Feb. 22, 2018

(65) Prior Publication Data

US 2019/0254545 A1    Aug. 22, 2019

(51) Int. Cl.
| | | |
|---|---|---|
| A61B 5/04 | (2006.01) | |
| A61B 5/0488 | (2006.01) | |
| A61B 5/00 | (2006.01) | |
| A61B 34/30 | (2016.01) | |

(52) U.S. Cl.
CPC ...... *A61B 5/04001* (2013.01); *A61B 5/04882* (2013.01); *A61B 5/4041* (2013.01); *A61B 5/4893* (2013.01); *A61B 34/30* (2016.02)

(58) Field of Classification Search
CPC .............. A61B 5/04001; A61B 5/4041; A61B 5/04882; A61B 34/30; A61B 5/4893
See application file for complete search history.

(56) References Cited

U.S. PATENT DOCUMENTS

| | | | |
|---|---|---|---|
| 6,091,995 A | 7/2000 | Ingle et al. | |
| 2003/0236557 A1* | 12/2003 | Whitehurst | A61N 1/0556 607/39 |
| 2008/0177339 A1* | 7/2008 | Bolea | A61N 1/05 607/3 |
| 2008/0183238 A1 | 7/2008 | Chen | |
| 2008/0194970 A1* | 8/2008 | Steers | A61B 5/0059 600/476 |
| 2015/0297139 A1* | 10/2015 | Toth | A61B 18/18 600/381 |

FOREIGN PATENT DOCUMENTS

| | | |
|---|---|---|
| WO | 2012109760 A1 | 8/2012 |
| WO | 2017059870 A1 | 4/2017 |

* cited by examiner

*Primary Examiner* — Amanda K Hulbert
*Assistant Examiner* — Natasha Patel
(74) *Attorney, Agent, or Firm* — Patent Office of Dr. Chung Park

(57) ABSTRACT

Systems and methods for mapping a cavernous nerve near an organ. The system includes: one or more processors; and a memory that is communicatively coupled to the one or more processors and stores one or more sequences of instructions, which when executed by one or more processors causes steps to be performed comprising: applying an excitation signal to an electrode at a tip of an laparoscope, the tip being configured to contact a point on a tissue near an organ; responsive to the excitation signal, measuring a change in a signal from a pair of electrodes configured to be installed on the penis, the change in the signal being associated with an erectile function of the penis; and based on the change in the signal from the pair of electrodes, determining a distance between the point on the tissue and a cavernous nerve near the organ.

20 Claims, 15 Drawing Sheets

MAPPING CAVERNOUS NERVES DURING SURGERY

TECHNICAL FIELD

The present invention relates to monitoring and mapping erectile nerves to preserve the erectile nerves, more particularly, to systems and methods for monitoring, mapping and preserving cavernous nerves during a surgery in the pelvic region.

DESCRIPTION OF THE RELATED ART

With the advent of surgical technologies, surgeries are performed on various organs in the pelvic region. For instance, prostate cancer is one of the most common solid organ cancers in men and the fifth leading cause of cancer-related death in men. Radical prostatectomy (RP), which refers to removing entire portion of the prostate from a patient, is considered as a standard surgical treatment for clinically localized prostate cancer. FIG. 1 shows a diagram of organs and nerves of the male pelvic region. Typically, the neurovascular bundle (NVB), which collectively refers to the combination of nerves, arteries, veins, and lymphatics in the body that travel together, surrounds the prostate and the physicians dissect (separate) the NVB from the prostate during the RP process.

The NVB is embedded in the periprostatic neurovascular tissue (or, shortly tissue) surrounding the prostate, where the NVB includes right and left cavernous nerves that are located on the right and left sides of the prostate, respectively. (Hereinafter, the terms tissue and NVB are used interchangeably.) The cavernous nerves facilitate the penile erection by controlling the blood flow to the corpora cavernosa (CC). Typically, it is difficult to locate the cavernous nerves embedded in the tissue during the RP process and as such, the physician may inadvertently damage the cavernous nerves during the RP process. In such a case, erectile dysfunction (ED) may follow and remain as a significant quality of life issue for men undergoing prostatectomy.

In the conventional systems, the physicians may check integrity of the cavernous nerves by penile plethysmography (PPG) or phallometry, wherein PPG measures blood flow to the penis in response to inter-operative electric stimulation during surgery. The most commonly reported methods of conducting penile plethysmography involve the measurement of the circumference of the penis with a mercury-in-rubber or electromechanical strain gauge, or the volume of the penis with an airtight cylinder and inflatable cuff at the base of the penis.

RP is not the only procedure that can damage the cavernous nerves. In fact, the cavernous nerves are exposed to potential damages when the surgical tools, such as knife or scissor, are operated near the cavernous nerves. However, the conventional PPG techniques cannot accurately map/locate the cavernous nerves and accordingly, there is a need for efficient systems and methods for monitoring and mapping cavernous nerves during a surgery in the pelvic region for preservation of erectile function.

SUMMARY OF DISCLOSURE

In embodiments, a system for mapping a cavernous nerve near an organ includes: one or more processors; and a memory that is communicatively coupled to the one or more processors and stores one or more sequences of instructions, which when executed by one or more processors causes steps to be performed comprising: applying an excitation signal to an electrode at a tip of an laparoscope, the tip being configured to contact a point on the tissue near an organ; responsive to the excitation signal, measuring a change in a signal from a pair of electrodes configured to be installed on the penis, the change in the signal being associated with an erectile function of the penis; and based on the change in the signal from the pair of electrodes, determining a distance between the point on the tissue and a cavernous nerve near the organ.

In embodiments, a method for mapping a cavernous nerve near an organ includes the steps of: applying an excitation signal to an electrode at a tip of an laparoscope, the tip being configured to contact a point on a tissue near an organ; responsive to the excitation signal, measuring a change in a signal from a pair of electrodes configured to be installed on the penis, the change in the signal being associated with an erectile function of the penis; and based on the change in the signal from the pair of electrodes, determining a distance between the point on the tissue and a cavernous nerve near the organ.

In embodiments, a non-transitory computer-readable medium or media includes one or more sequences of instructions which, when executed by one or more processors, causes steps to be performed comprising: applying an excitation signal to an electrode at a tip of an laparoscope, the tip being configured to contact a point on a tissue near an organ; responsive to the excitation signal, measuring a change in a signal from a pair of electrodes configured to be installed on the penis, the change in the signal being associated with an erectile function of the penis; and based on the change in the signal from the pair of electrodes, determining a distance between the point on the tissue and a cavernous nerve near the organ.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components that may be implemented in software, hardware, or a combination thereof.

It shall also be noted that the terms "coupled" "connected" or "communicatively coupled" shall be understood to include direct connections, indirect connections through one or more intermediary devices, and wireless connections.

Furthermore, one skilled in the art shall recognize: (1) that certain steps may optionally be performed; (2) that steps may not be limited to the specific order set forth herein; and (3) that certain steps may be performed in different orders, including being done contemporaneously.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. The appearances of the phrases "in one embodiment," "in an embodiment," or "in embodiments" in various places in the specification are not necessarily all referring to the same embodiment or embodiments.

Figure 1:
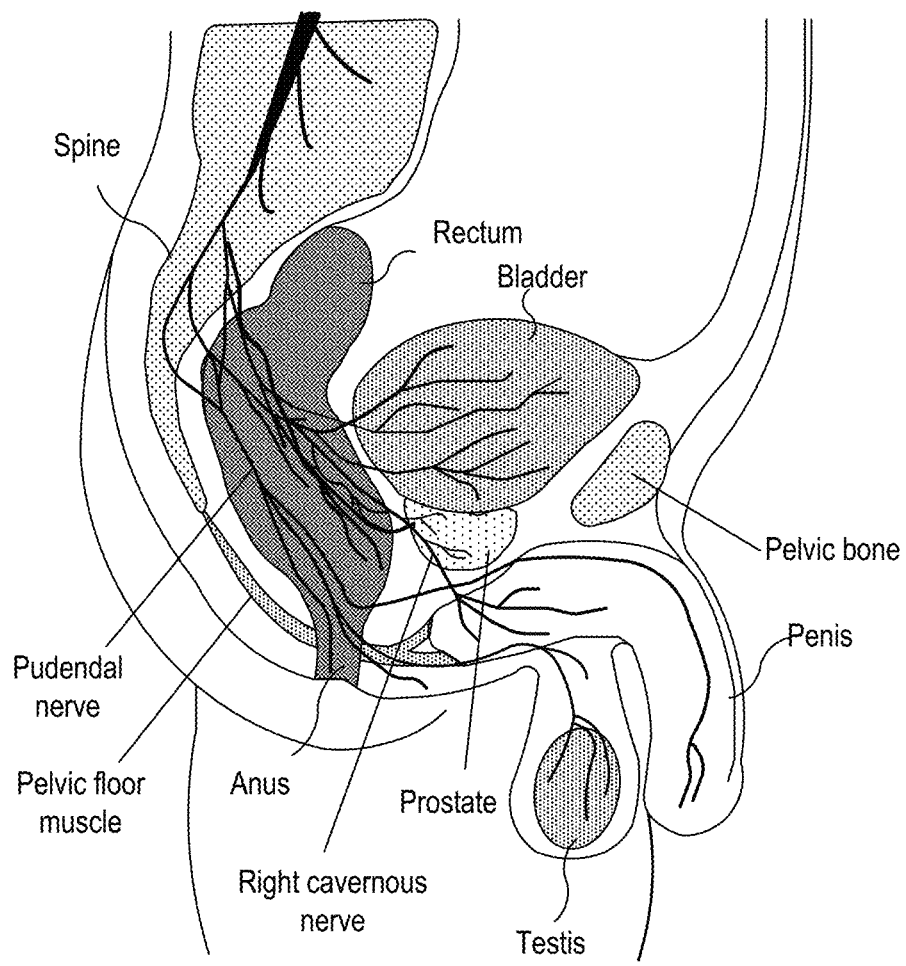
FIG. 1 shows a schematic diagram of organs and nerves of the male pelvic region.
Figure 2:
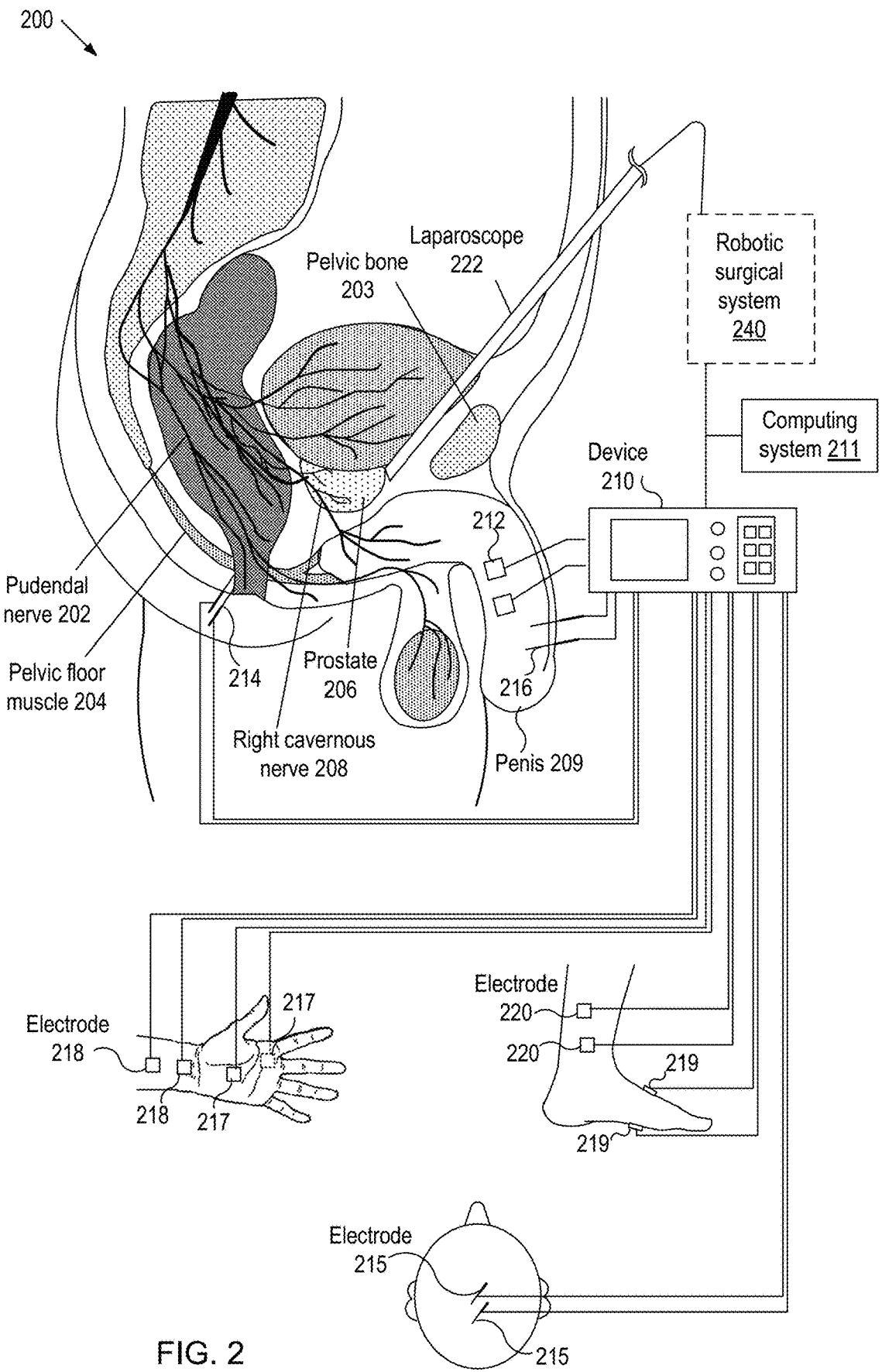
FIG. 2 shows a schematic diagram of a system for monitoring and mapping cavernous nerves during the RP process according to embodiments of the present invention.

FIG. 2 shows a schematic diagram of a system 200 for monitoring and mapping cavernous nerves during the radical prostatectomy according to embodiments of the present invention. As depicted, the system 200 may include: a device 210 for operating various electrodes attached to or inserted into a patient's body; one or more electrodes 212-220 electrically coupled to the device 210; at least one laparoscope 222 having a tip inserted into the patient's body for performing various operations; and optionally, a robotic surgical system 240. In the present document, the monitoring and mapping of cavernous nerves are described in conjunction with the robot-assisted laparoscopic radical prostatectomy. However, it should be apparent to those ordinary skill in the art that the monitoring and mapping may be performed as an intraoperative process during any other surgical procedures.

In embodiments, the robot surgical system 240 may include a surgeon's console (not shown in FIG. 2) that is typically in the same room as the patient, and a patient-side cart with several interactive robot arms controlled from the console. Some of the arms (not shown in FIG. 2) may be for holding and maneuvering surgical tools, such as scissors, bovie knives, scalpels, so on. In embodiments, one of the robot arms may hold the laparoscope 222 having a catheter, where the tip of the catheter is inserted into the patient's body and has an electrode for applying electrical signals to a target organ/tissue. In embodiments, the laparoscope 222 may be an endoscopic catheter that allows direct visualization of the patient internal organs as well as application of electrical signals through the tip (or equivalently probe) electrode. In alternative embodiments, a separate endoscopic catheter may be inserted into the patient's body for visualization while the surgeon operates the laparoscope 222 to apply electrical signals to the target organ/tissue via the tip electrode. In yet alternative embodiment, the laparoscope 222 may be inserted and operated to apply the electrical signal only. More detailed description of the laparoscope 222 is given below.

In embodiments, the device 210 may include one or more control panels and/or user interfaces (such as control knobs or switches) that allow the operator to control the device. In embodiments, the device 210 may be electrically coupled to the laparoscope 222 directly. More specifically, the device 210 may be electrically coupled to the electrode contained in the laparoscope 222, where the electrode may be used to apply excitation signals to the target tissue. In alternative embodiments, the device 210 may be electrically coupled to laparoscope via the robot surgical system 240, i.e., the laparoscope 222 may be handled by an arm of the robotic surgical system 240. In either case, the device 210 may provide electrical signals through the electrode at the tip of the laparoscope 222.

In embodiments, the device 210 may be electrically coupled to a computing system 211, such as notebook, server, laptop computer, so on. In embodiment, the device 210 may be combined with the computing system 211 as one integral body.

In embodiments, the device 210 may be electrically coupled to one or more electrodes 212-220. It is noted that the electrodes 212-220 may be used to apply electrical signal to the patient's body as well as measure changes in the voltage between two electrodes, where the voltage change may commensurate with the change in the electrical impedance of the human body between the electrodes and the change in the impedance may correspond to the change in the physical states of the patient's body. In embodiments, two or more surface electrodes 212 may be attached to the skin of the penis 209 and measure the variation of electrical impedance of the body between the electrodes 212. Since the electrical impedance of the body between the electrodes 212 may change as a portion of the body between the electrodes changes with the blood being pooled in the penis, the surface electrodes 212 may be used to detect/measure the erectile function of the penis. In embodiments, the surface electrodes 212 may be also used to apply an excitation signal to the penis, and the signals from other electrodes in response to the excitation signal may be measured as CC-EMG signals.

In embodiments, two or more needle electrodes 216 may be inserted into each corpus cavernosum. Similar to the surface electrodes 212, the electrical impedance of the body between the needle electrodes 216 may change as the amount of the blood in the corpus cavernosum changes. As such, the needle electrodes 216 may be used to detect/measure the activity (i.e., erectile function) of the corpus cavernosum.

Figure 4A:
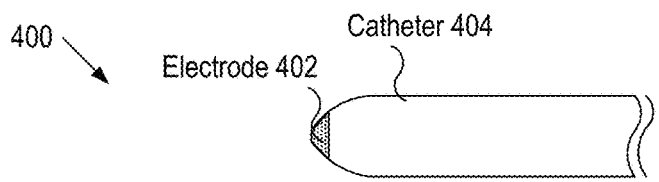
FIG. 4A shows an enlarged view of a laparoscope according to embodiments of the present invention.

To prevent injury to the cavernous nerves during the RP process that includes dissection (separation) of the prostate 206 from the surrounding tissue and neurovascular bundle, the exact locations of the cavernous nerves need to be mapped. In embodiments, to map (locate) the cavernous nerves in the surrounding tissue, the operator of the device 210 or the robot arm of the system 240 may position the tip of the laparoscope 222 to a point on the tissue where the cavernous nerves are likely to be. Then, the device 210 may apply an electrical excitation signal to the tissue through the probe electrode at the tip of the laparoscope 222. FIG. 4A shows an enlarged view of a laparoscope 400 according to embodiments of the present invention. As depicted, the laparoscope 400 may include a catheter 404 and a probe electrode 402 located at the tip portion of the catheter 404.

In embodiments, if the electrical signal from electrodes 212 (and/or 216) shows a change in response to the excitation signal applied to the probe electrode 402, the device 210 may determine that the cavernous nerve is located near the tip of the laparoscope 400. In embodiments, the magnitude of the change in the electrical signals from the electrodes 212 (and/or 216) may be used to determine whether the tip of the laparoscope 400 is located near the cavernous nerve or not.

Typically, each cavernous nerve may have multiple branches that run through the tissue surrounding the prostate 206. As such, in embodiments, the device 210 may repeatedly send the excitation signals while positioning the tip of the laparoscopic instrument 222 at different locations on the tissue that surrounds the prostate 206. Then, by measuring the electrical signals from the electrodes 212 (and/or 216) in response to the excitation signals, the device 210 may map the distribution of the cavernous nerves in the tissue around the prostate 206.

In embodiments, right after the surgeon competes the dissection of the prostate 206 from the surrounding tissue but before the prostate is extracted from the patient's body, the device 210 may map the distribution of the cavernous nerves on the prostate base surface, where the prostate base surface refers to the surface of the surrounding tissue that was in direct contact with the prostate before the dissection.

As discussed above, the left and right NVBs may be located on the five and seven o'clock directions of the prostate 206, respectively, when viewed from the pelvic bone 203. In embodiments, individual variations in the locations of the left and right cavernous nerves exist and, as such, exact locations of the left and right cavernous nerves should be checked individually. In embodiments, the device 210 may map the cavernous nerves in the tissue/NVBs before and after the surgeon extracts the prostate 206.

Figure 4B:
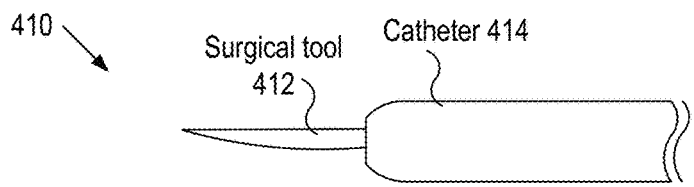
FIG. 4B shows an enlarged view of a laparoscope according to embodiments of the present invention.

In embodiments, the device 210 may issue a warning signal to the surgeon/operator of the device 210 if it is determined that the cavernous nerve is too close to the tip of the instrument 222. In embodiments, the tip of laparoscope 222 may include a knife, where the knife may be used as a surgical tool to dissect the prostate 206 from the surrounding tissue/NVBs. In embodiments, the knife may be formed of electrically conducting material and used as a probe electrode. FIG. 4B shows an enlarged view of a laparoscope 410 according to embodiments of the present invention. As depicted, the instrument 410 may include a catheter 414 and a surgical tool 412, such as knife or scissor, located at the tip portion of the catheter. During the RP process, the surgeon may bring the tool 412 into contact with the tissue and the device 210 may send an excitation signal through the tool 412. Then, the electrical signals from the electrodes 212 (or 216) may be measured to determine the distance between the tool 412 and the cavernous nerve 208. In embodiments, if the peak amplitude (such as 506) of the electrical signals from the electrodes 212 (or 216) exceeds a threshold value, the device 210 determined that the cavernous nerves is too close to the tip of the tool 412, the device 210 may issue a proper warning signal and/or feedback to the surgeon so that the surgeon does not cut the tissue at the current location of the tool 412, to thereby preserve the cavernous nerve. In embodiments, the device 210 may have a speaker that may issue an audio warning signal to the surgeon. In embodiments, the device 210 may have a display for displaying a visual warning signal on the display 308. It is noted that the warning signal may include other suitable types of feedback to the surgeon.

Figure 4C:
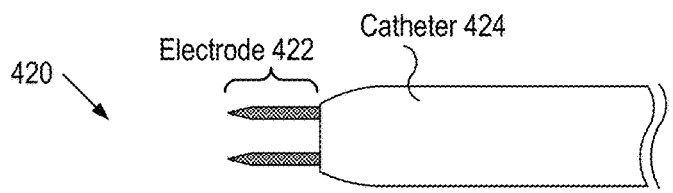
FIG. 4C shows an enlarged view of a laparoscope according to embodiments of the present invention.
Figure 4D:
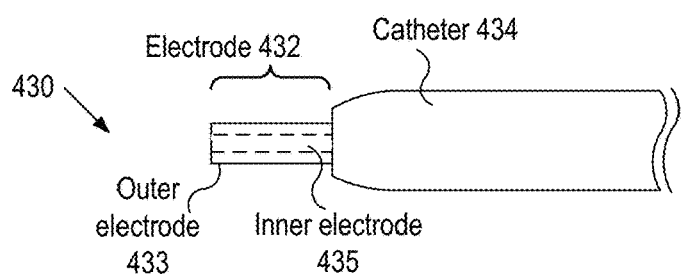
FIG. 4D shows an enlarged view of a laparoscope according to embodiments of the present invention.

In FIGS. 4A and 4B, the electrical excitation signal applied to the tissue through the tip electrodes 402 and 412 may be unipolar signal, i.e., the tip electrodes are unipolar electrodes. In embodiments, the electrical excitation signals may be bipolar signals. FIG. 4C shows an enlarged view of a laparoscope 420 according to embodiments of the present invention. As depicted, a two-prong bipolar electrode 422 may be formed at the tip portion of the catheter 424 so that a bipolar signal may be applied to a point on the tissue that comes in contact with the electrode 422. FIG. 4D shows an enlarged view of a laparoscope 430 according to embodiments of the present invention. As depicted, a concentric bipolar electrode 432 may include an outer electrode 433 and an inner electrode 435 and may be formed at the tip portion of the catheter 434 so that a bipolar signal may be applied to a point on the tissue that comes in contact with the bipolar electrode 432. It is noted that the two-prong bi-polar electrode 422 may contact the tissue at two points. In such a case, the point refers to the midpoint of the ends of the two prongs.

Referring back to FIG. 2, the electrodes 217-220 may be electrically coupled to the device 210. In embodiments, a pair of surface electrodes 217 may be attached to the palm and backside of the hand, where the signal from the electrodes 217 may measure the variation of the electrical impedance of the hand therebetween, i.e., the electrodes 217 may be sensor electrodes. In embodiments, another pair of surface electrodes 218 may be attached to the wrist along the median nerve, where an electrical excitation signal may be applied through the electrodes 218 so as to stimulate the median nerve in the wrist, i.e., the electrodes 218 may be excitation electrodes.

In embodiments, a pair of surface electrodes 219 may be attached to the bottom and backside of the foot, where the signal from the electrodes 219 may measure the variation of electrical impedance of the foot therebetween, i.e., the electrodes 219 may be sensor electrodes. In embodiments, another pair of surface electrodes 220 may be attached to the ankle along the tibial nerve, where an electrical excitation signal may be applied through the electrodes 220 so as to stimulate the tibial nerve in the ankle, i.e., the electrodes 220 may be excitation electrodes.

FIG. 2 shows the electrodes 212, 214, 216, 217, 218, 219, and 220 installed on one side of the patient. However, the same electrodes may be installed on the other side of the patient. For instance, a first pair of surface electrodes 212 may be attached to the right hand side of the penis 209 and a second pair of surface electrodes 212 may be attached to the left hand side of the penis 209. In another example, the two pairs of surface electrodes 217 and 218 may be attached to the right hand of the patient and another two pairs of surface electrodes 217 and 218 may be attached to the left hand.

Figure 3:
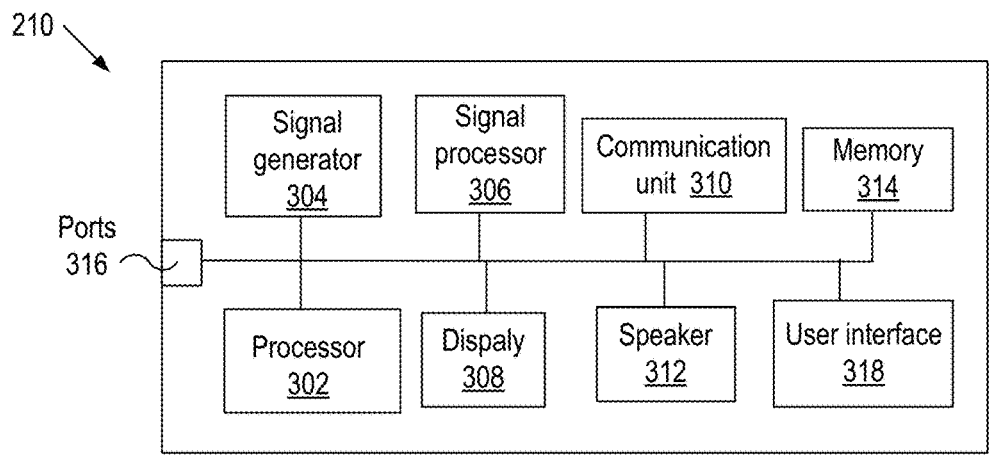
FIG. 3 shows a schematic diagram of a device for monitoring and mapping cavernous nerves according to embodiments of the present invention.

FIG. 3 shows a schematic diagram of the device 210 for monitoring and mapping cavernous nerves according to embodiments of the present invention. In embodiments, the device 210 may be a computing device and may include: a processor 302, such as a microprocessor, for operating the components of the device; a signal generator 304 for generating and sending electrical signals to one or more of the electrodes 212-220; signal processor 306 for receiving electrical signals from one or more of the electrodes 212-220 and processing (such as filtering noise and amplifying signal, etc.) the electrical signals; a communication unit 310 for communicating data to external devices, such as robot surgery system 240 and the computing system 211 via wires and/or wireless channels; a display 308 for displaying the signals from the electrodes 212-220 and/or messages; a memory 314 for storing data; a speaker 312 for displaying audio signals to the surgeon/operator of the device; one or more ports 316 for accepting various terminals, such as power cable, USB, so on; and a user interface 318 for accepting input control signals from the user of the device. In embodiments, the laparoscope 222 may include an endoscopic catheter that sends images of the internal organs of the patient, and the display 308 may display the images while the surgeon is performing the RP process using the robotic surgery system 240. In embodiments, the user interface 316 may accept the input from the user, such as turning knobs, touching control panels, typing a keyboard or moving a mouse.

It is noted that each component in the device 210 may include one or more electrical elements/circuits. For instance, the signal generator 304 may include a waveform generator and amplifier for adjusting the amplitude of the generated waveform. In the following figures, the electrical excitation signals may be applied through one or more of the electrodes 212-220, where the signal generator 304 may send the excitation signal to the electrodes.

It is noted that some of the components of the device 210 may be implemented in the computing system 211. For instance, the display 308 may be implemented in the computing device 211 instead of the device 210. It is also noted that one or more additional components may be implemented in the device 210. For instance, a battery that provides electrical power to the components of the device 210 may be implemented in the device 210.

Figure 5:
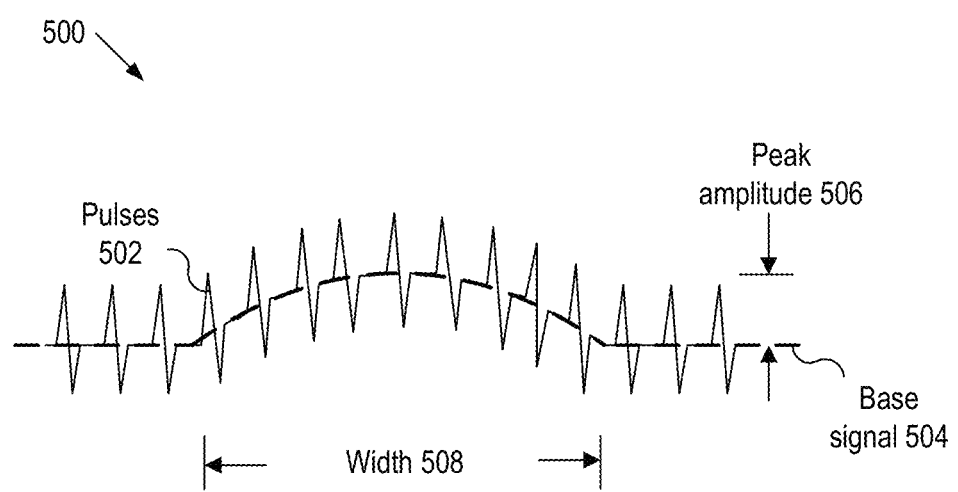
FIG. 5 shows an exemplary signal from an electrode according to embodiments of the present invention.

FIG. 5 shows an exemplary signal 500 from the electrodes 212 (or 216) in response to an external excitation signal according to embodiments of the present invention. As depicted, the signal 500 may include pulses 502 superimposed on the base signal 504, where the pulses 502 show the variation of the electrical impedance of the body between two electrodes 212 (or 216) due to the blood flow through the corpus cavernosum by the heart. In embodiments, the base signal 504 may represent portions of the signal between the pulses 502. In embodiments, in response to an excitation signal(s), the base signal 504 may show a change that has the width 508 and peak amplitude 506, where the width and peak amplitude may vary depending on various parameters, such as the type of external excitation signal and the location where the external excitation signal is applied.

In embodiments, a minimum threshold of the width 508 may be defined to filter out noises at high frequencies. For instance, the device 210 may ignore the fluctuation of the base signal if the width 508 is below the minimum threshold. In embodiments, the device 210 may obtain two base signals before and after applying the external excitation signal and compare the base signals to determine whether the corpus cavernosum responds to the external excitation signal. For instance, when an excitation signal is applied after the RP process, the peak amplitude may be close to zero if the cavernous nerves are inadvertently severed during the RP process. In another example, when an excitation signal is applied after the RP process, the width and peak amplitude would be similar to those before the RP process if the cavernous nerves are intact.

In embodiments, the peak amplitude may get larger if the point where the probe electrode 402 is located gets closer to the cavernous nerve. In embodiments, a threshold value for the peak amplitude 506 may be set in advance. Then, when the peak amplitude exceeds the preset threshold value in response to an excitation signal, the device 210 may determine that the surgical tool 412 is too close to the cavernous nerve and speaker 312 may issue a warning signal to the surgeon so that the surgeon would not cut the tissue at the point where the surgical tool 412 is located.

Figure 6:
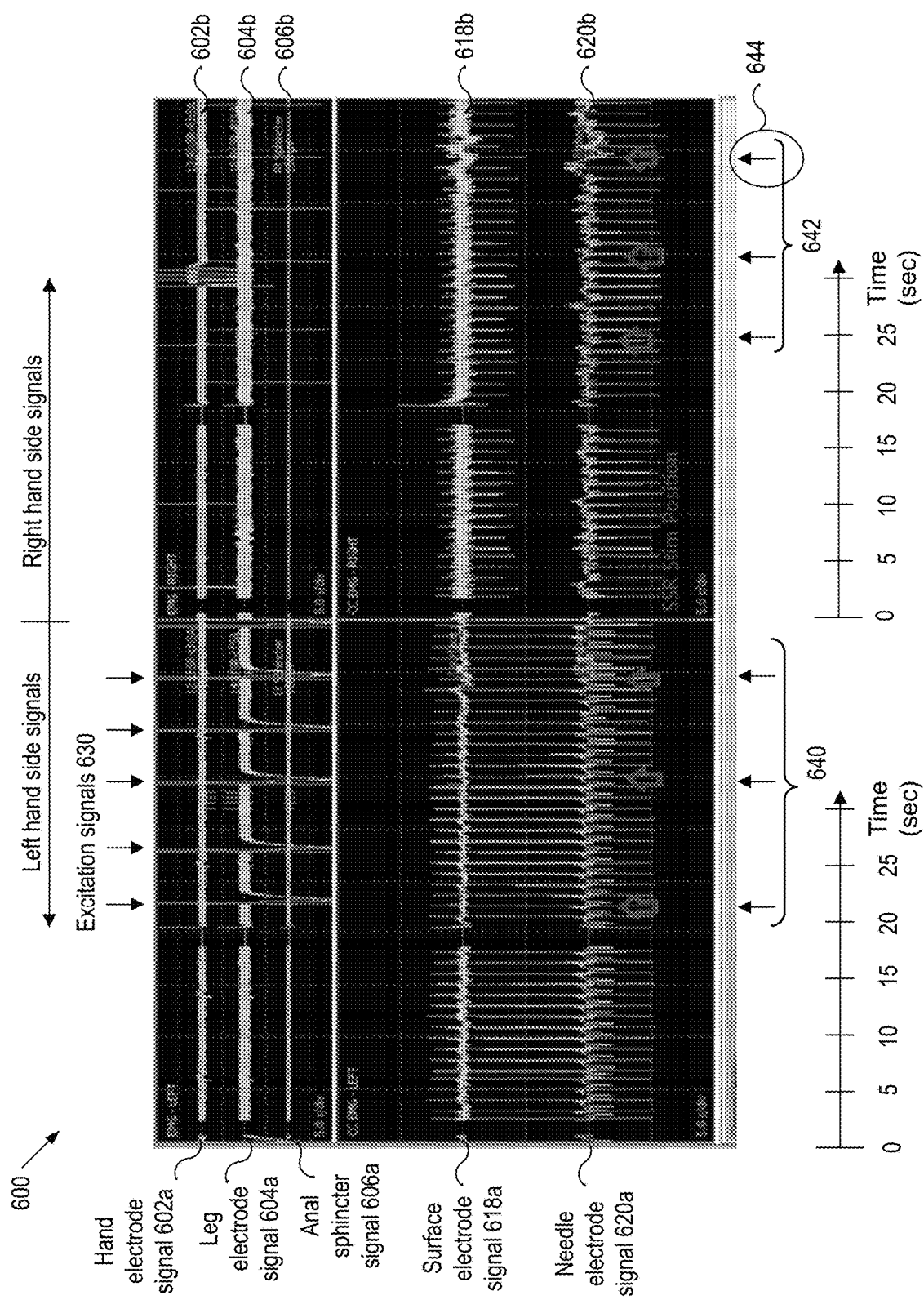
FIG. 6 shows an exemplary screenshot that includes skin response (SSR) corpus cavernosum electromyography (CC-EMG) signals according to embodiments of the present invention.

FIG. 6 shows an exemplary screenshot 600 that includes SSR CC-EMG signals according to embodiments of the present invention. As depicted, the left half of the screenshot 600 show signals from electrodes mounted on the left hand side of the patient while the right half of the screenshot 600 show signals from electrodes mounted on the right hand side of the patient. More specifically, the plots 602a, 604a, 606a, 618a, and 620a are signals from the pair of surface electrodes 217 on the left hand, the pair of surface electrodes 219 on the left foot, the pair of needle electrodes 214 inserted in the left hand side of the external anal sphincter muscle, the pair of surface electrodes 212 on the left hand side skin of the penis 209, and the pair of needle electrodes 216 inserted into the left corpus cavernosum, respectively. Similarly, the plots 602b, 604b, 606b, 618b, and 620b are signals from the pair of surface electrodes 217 on the right hand, the pair of surface electrodes 219 on the right foot, the pair of needle electrodes 214 inserted in the right hand side of the external anal sphincter muscle, the pair of surface electrodes 212 on the right hand side skin of the penis 209, and the pair of needle electrodes 216 inserted into the right corpus cavernosum, respectively.

The plots in the screenshot 600 represent the sympathetic skin response (SSR) corpus cavernosum electromyography (CC-EMG), where SSR CC-EMG shows cavernous electrical activity in response to an excitation signal applied to the pair of electrodes 220 on the ankle of the patient. In the screenshot 600, the plots 602a, 602b, 604b, 606a, 606b, 618a, 618b, 620a and 620b are signals from the corresponding electrodes when several excitation signals 630 are applied to the pair of electrodes 220 on the left ankle. As depicted, the various portions of the plot 620a indicated by the arrows 640 may indicate the locations where the cavernous electrical activity of the left corpus cavernosum is expected in response to the excitation signals 630 while the various portions of the plot 620b indicated by the arrows 642 indicate the locations where the cavernous electrical activity of the right corpus cavernosum is expected in response to the excitation signals 630. As the CC-EMG signals show distinct cavernous electrical activity at point indicated by the arrow 644, the device 210 may determine that the corpora cavernosa function properly. In embodiments, as discussed above in conjunction with FIG. 5, the device 210 may measure the change in the base signal of the plot 620b, and determine that the right corpus cavernosum functions properly if the width and peak amplitude of the base signal at the arrow 644 exceed preset threshold values.

In embodiments, one or more subdermal needle electrodes 215 may be inserted into the scalp in the sagittal plane (Cz-Fz montage) of the patient and electrically coupled to the device 210. In embodiments, to measure the electrical activity of the brain that results from the stimulation of touch, the device 210 may apply an electrical excitation signal to the surface electrodes 212 and measure the electrical signal (i.e., pudendal somatosensory evoked potentials signal) from the electrodes 215 in response to the excitation signal. During the RP process, the device 210 may repeatedly send electrical excitation signals to the electrodes 212 and check the electrical signals from the electrodes 215 to monitor the somatosensory system function of the patient.

Figure 7:
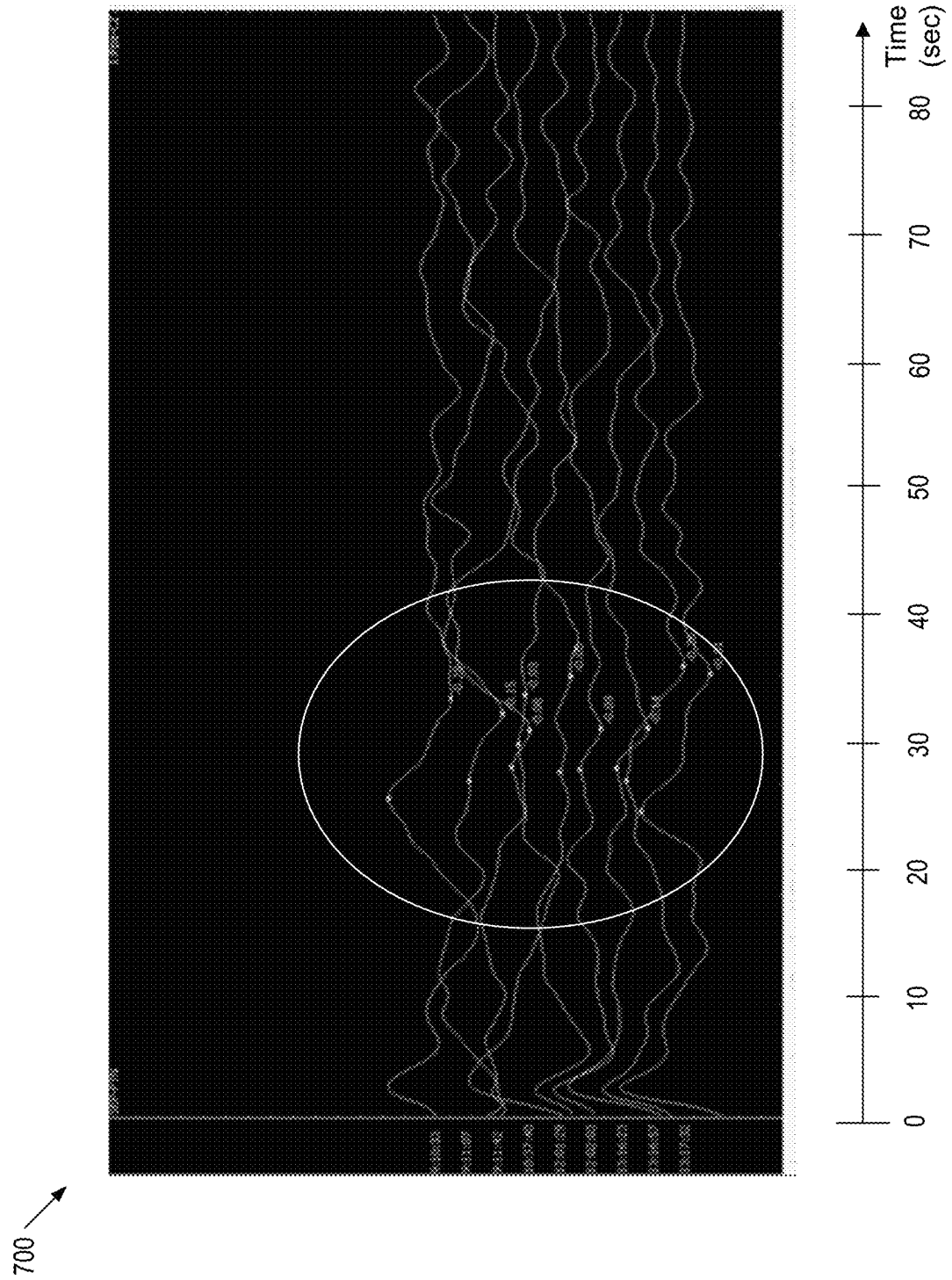
FIG. 7 shows an exemplary screenshot that includes pudendal somatosensory evoked potentials (SEP) signals according to embodiments of the present invention.

FIG. 7 shows an exemplary screenshot 700 that includes pudendal somatosensory evoked potentials (SEP) signals according to embodiments of the present invention. In embodiments, the plots in the screenshot 700 show electrical signals from the subdermal needle electrodes 215 inserted into the coronal skin of the patient.

As depicted, each pudendal SEP signal shows a distinct and consistent responses at a constant latency elicited by an electrical excitation signal applied to the surface electrodes 212. It is noted that the plots in FIG. 7 are generated by applying electrical excitation signals at different times and shifting the obtained pudendal SEP signals on the time axis such that each SEP signal begins at the origin of the time axis.

In embodiments, the presence and consistency of pudendal SEP indicate that the sensory nerve system of the patient is intact. In embodiments, to monitor a potential injury to the sensory nerve system, the pudendal SEP signals may be repeatedly measured on a regular basis during the RP process.

Figure 8:
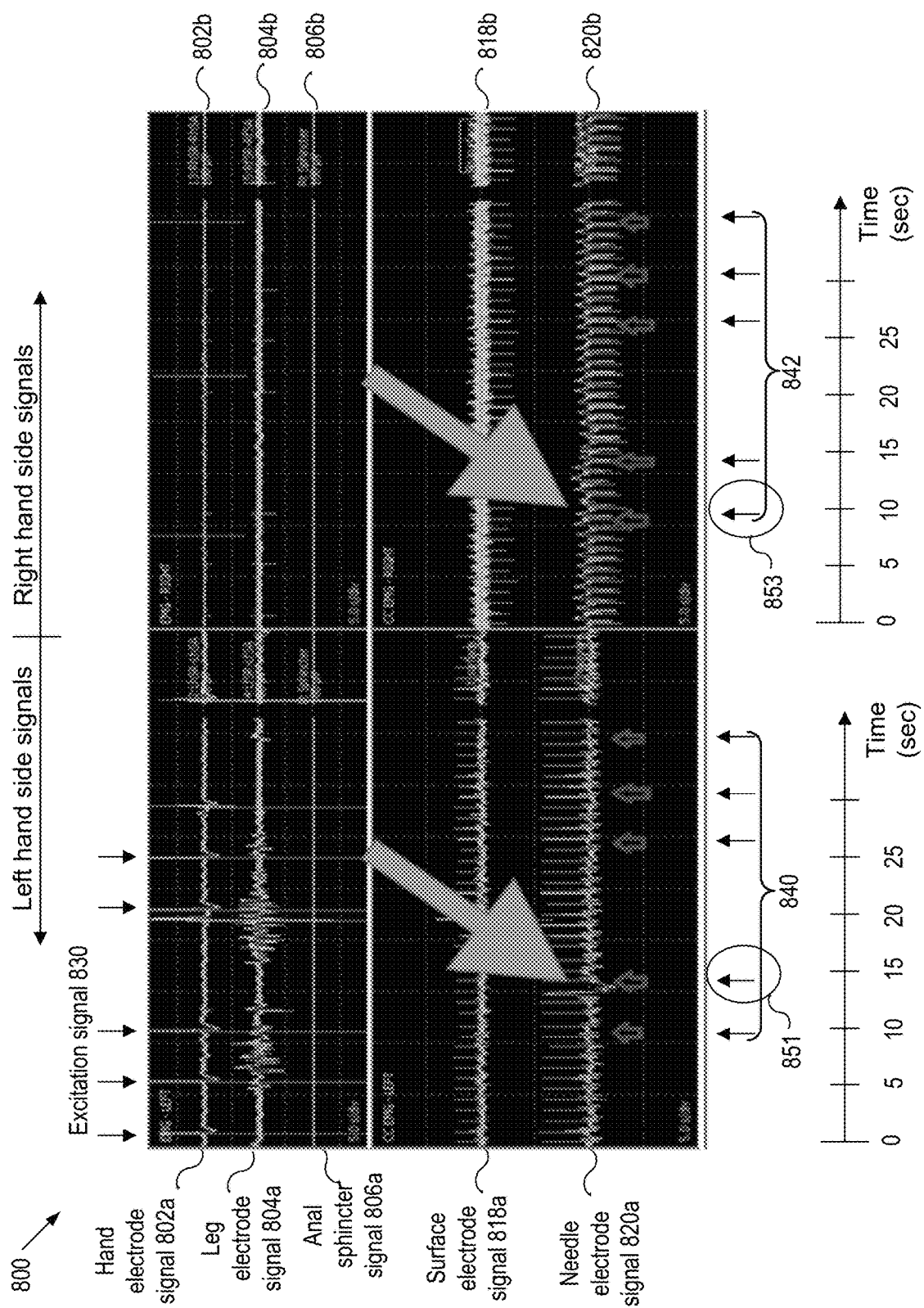
FIG. 8 shows an exemplary screenshot that includes SSR CC-EMG signals according to embodiments of the present invention.

FIG. 8 shows an exemplary screenshot 800 that includes sympathetic skin response (SSR) corpus cavernosum electromyography (CC-EMG) signals according to embodiments of the present invention. The plots in the screenshot 800 are similar to the plots in the screenshot 600, with the difference that the excitation signals 830 are applied to the surface electrodes 218 on the left wrist. The plots 818a, 818b, 820a, and 820b in the screenshot 800 may represent the SSR CC-EMG signals, where the SSR CC-EMG signals reflect change of impedance of corpus cavernosum from vasomotor activity in response to excitation signals 830. As depicted, the arrows 840 (and 842) may indicate the locations where the cavernous electrical activity of the left (and right) corpus cavernosum is expected in response to the excitation signals 830. As the SSR CC-EMG signals show distinct cavernous electrical activity at the locations indicated by the arrow 851 and 853, the device 210 may determine that the corpora cavernosa function properly.

Figure 9:
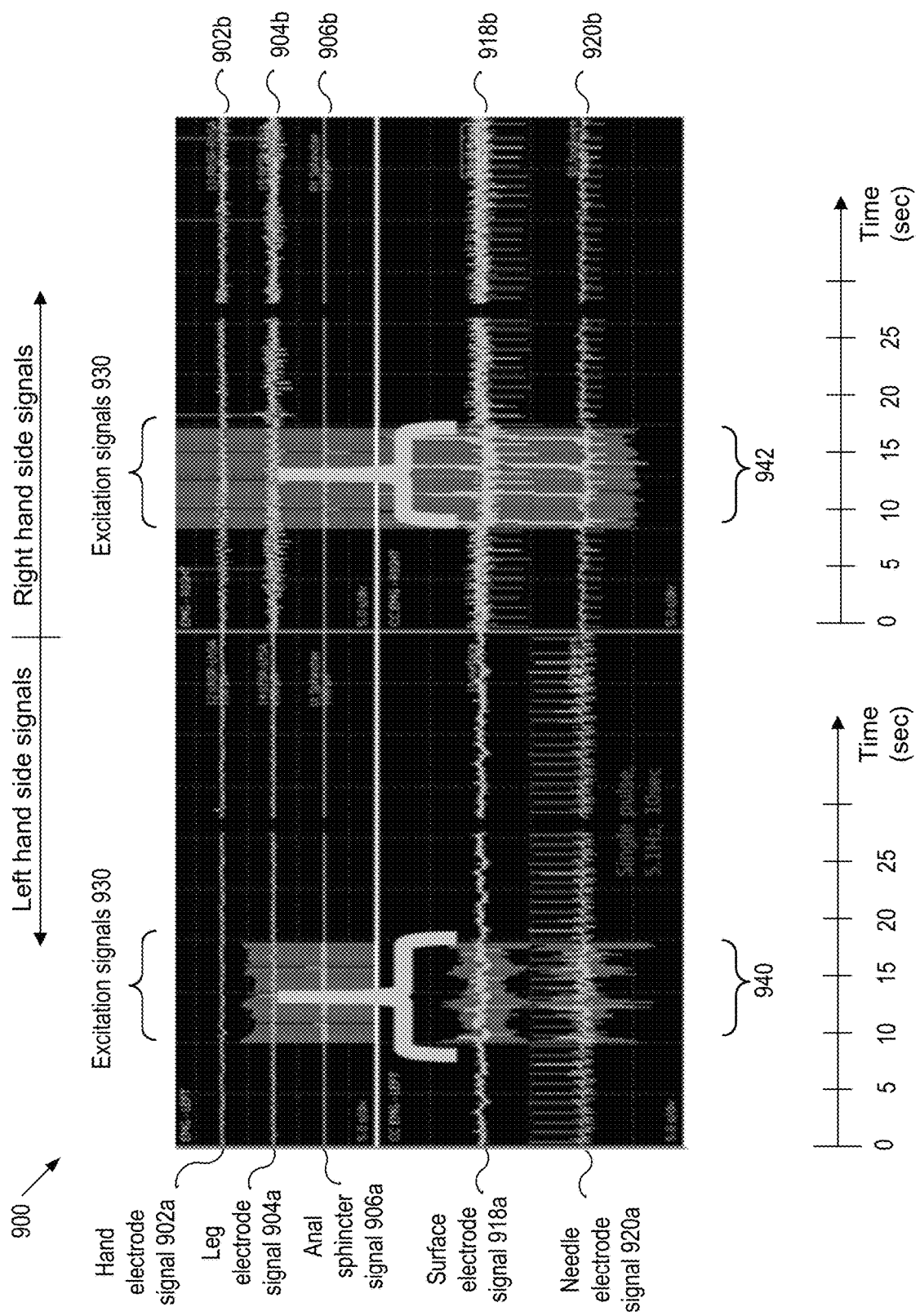
FIGS. 9-13 show exemplary screenshots that each include signals from various electrodes according to embodiments of the present invention.

FIG. 9 shows an exemplary screenshot 900 that includes signals from various electrodes according to embodiments of the present invention. In FIG. 9, the plots 902a (or 902b), 904a (or 904b), 906a (or 906b), 918a (or 918b), and 920a (or 920b) are signals from the pair of surface electrodes 217 on the left (or right) hand, the pair of surface electrodes 219 on the left (or right) foot, the pair of needle electrodes 214 inserted in the left (or right) external anal sphincter, the pair of surface electrodes 212 on the left (or right) hand side skin of the penis 209, and the pair of needle electrodes inserted into the left (or right) corpus cavernosum 216, respectively.

In FIG. 9, a train of electrical excitation pulses (such as sinusoidal or square waves) 930 is applied to the tip electrode 422 (or 432) of the laparoscope 420 (or 430) at 5.1 Hz for 10 seconds and the tip may be located on the tissue that is likely to contain the right cavernous nerve. Also, the train of electrical pulses 930 may be applied after bladder neck dissection, i.e., after prostate is dissected (separated) from the bladder and the tissue surrounding the prostate, but before the prostate is completely removed from the patient's body. As depicted, the portion 940 of the plots 918a (and 920a) shows the impedance change of body between the electrodes 212 (and 216) on the left hand side surface of the penis (and in the left corpus cavernosum), and the portion 942 of the plots 918b (and 920b) shows the impedance change of the body between the electrodes 212 (and 216) on the right hand side surface of the penis (and in the right corpus cavernosum). In embodiments, since each of the base signals of the four plots 918a, 918b, 920a, and 920b show sufficiently large peak amplitude and width in the portions 940 and 942, the device 210 may determine that the impedance change of the body between the electrodes 212 (and 216) is evident and the cavernous nerve is intact.

In embodiments, the change in the base signal of the plot 918a (918b, 920a or 920b) in response to the excitation signal 930 may be used to determine the distance between the location of the tip 422 (or 432) and the cavernous nerve 208, to thereby map the cavernous nerves. To determine the distance, the signal generator 304 may repeatedly send the excitation signals to the tip 422 (or 432) while the amplitude of the excitation signal 930 is progressively decreased to the value where the base signal does not show any change. Since the value is the minimum threshold for exciting the cavernous nerve, the device 210 use this threshold to determine the distance between the location of the tip 422 (or 432) and the cavernous nerve 208. In embodiments, the memory 314 may store information of the correlation between the threshold and the distance that is prepared in advance, and the device 210 may access the information to determine the distance corresponding to the currently measured minimum threshold. The device 210 may repeat this process while positioning the tip 422 at different locations on the tissue surrounding the prostate 206, to thereby map the cavernous nerve near the prostate.

In embodiments, the surgeon may use the laparoscope 410 during the RP process. In such a case, a train of excitation pulses that is similar to the signal 930 may be applied to a point on the tissue through the tip 412. If the magnitude of the peak amplitudes of the signals 918a (918b, 920a, or 920b) in response to the excitation signal exceeds a threshold value, the device 210 may determine that the distance between the point and the cavernous nerve 208 is too close and issue a warning sign to the surgeon so that the surgeon cut the tissue at the tip of the surgical tool 412.

Figure 10:
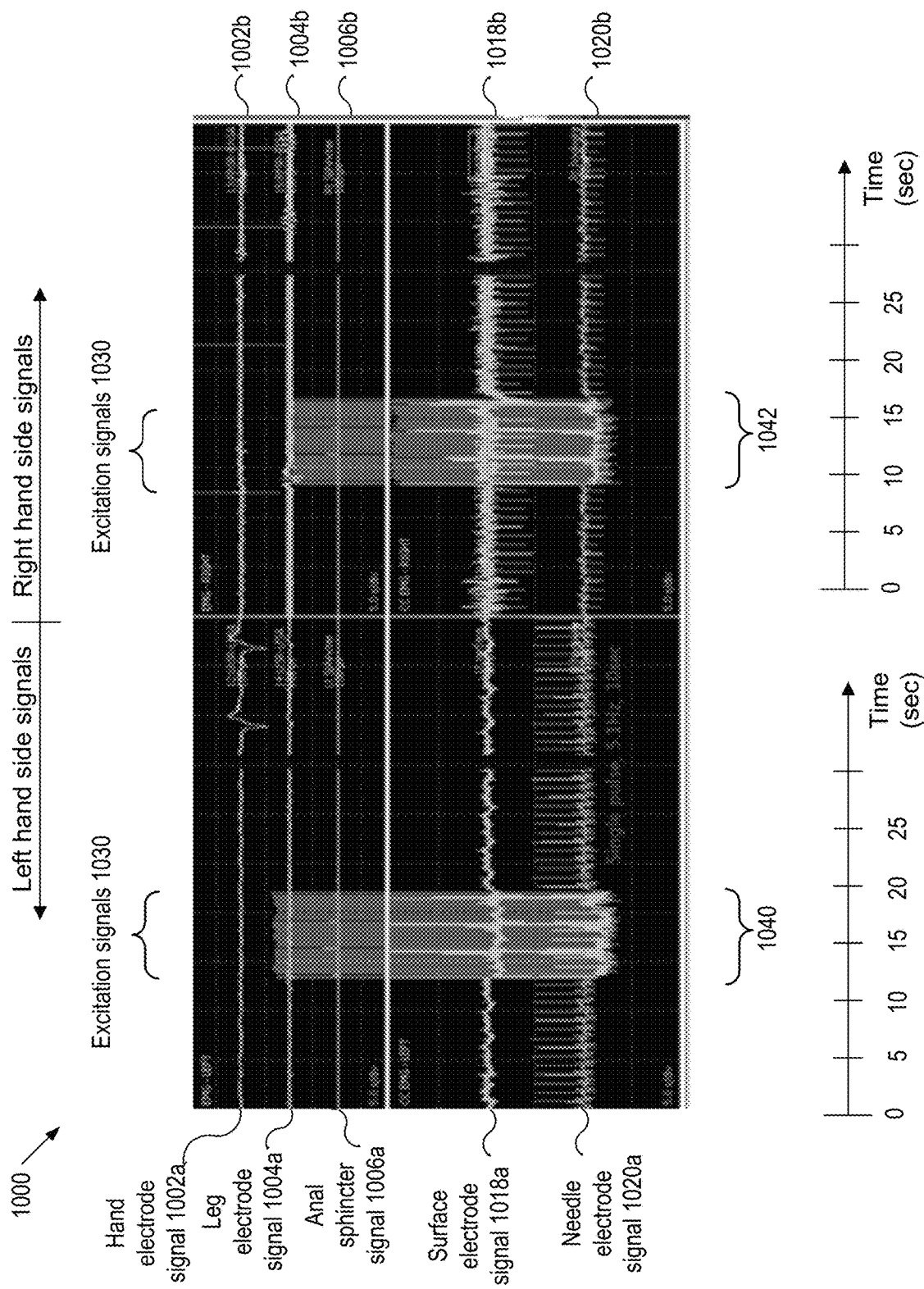

FIG. 10 shows an exemplary screenshot 1000 that includes signals from various electrodes according to embodiments of the present invention. In FIG. 10, the plots 1002a (or 1002b), 1004a (or 1004b), 1006a (or 1006b), 1018a (or 1018b), and 1020a (or 1020b) are signals from the pair of surface electrodes 217 on the left (or right) hand, the pair of surface electrodes 219 on the left (or right) foot, the pair of needle electrodes 214 inserted in the left (or right)

side of the external anal sphincter, the pair of surface electrodes 212 on the left (or right) hand side skin of the penis 209, and the pair of needle electrodes 216 inserted into the left (or right) corpus cavernosum, respectively.

In FIG. 10, a train of electrical excitation pulses 1030 is applied through the tip electrode 422 (or 432) of the laparoscope 420 (or 430) at 5.1 Hz for 10 seconds and the tip is located on the tissue that is likely to contain the left cavernous nerve. Also, the train of electrical pulses 1030 may be applied after bladder neck dissection, i.e., after prostate is dissected (separated) from the bladder and the tissue surrounding the prostate and after the prostate is completely removed from the patient's body. As depicted, the portion 1040 of the plots 1018*a* (and 1020*a*) shows the impedance change of the body between the electrodes 212 (and 216) on the left hand side of the penis (and in the left corpus cavernosum) and the portion 1042 of the plots 1018*b* (and 1020*b*) shows the impedance change of the body between the electrodes 212 (and 216) on the right hand side of the penis (and in the right corpus cavernosum).

The portion 1040 of the plot 1018*a* (and 1020*a*) shows the impedance change of the body between the electrodes 212 (and 216) on the left hand side of the penis (and in the left corpus cavernosum). The portion 1042 of the plot 1018*b* (and 1020*b*) shows the impedance change of the body between the electrodes 212 (and 216) on the right hand side of the penis (and in the right corpus cavernosum). In embodiments, since each of the base signals of the four plots 1018*a*, 1018*b*, 1020*a*, and 1020*b* show sufficiently large peak amplitude and width, the device 210 may determine that the impedance change of the body between the electrodes 212 (and 216) is evident and the left cavernous nerve is intact.

It is noted that the train of excitation pulses 930 (and 1030) in FIG. 9 (and FIG. 10) may be applied to a point on the tissue near the right cavernous nerve. In embodiments, if the plots 918, 920, 1018, and 1020 may show the similar changes in response to the excitation signals, the device 210 may determine that the right cavernous nerve may be intact.

Figure 11:
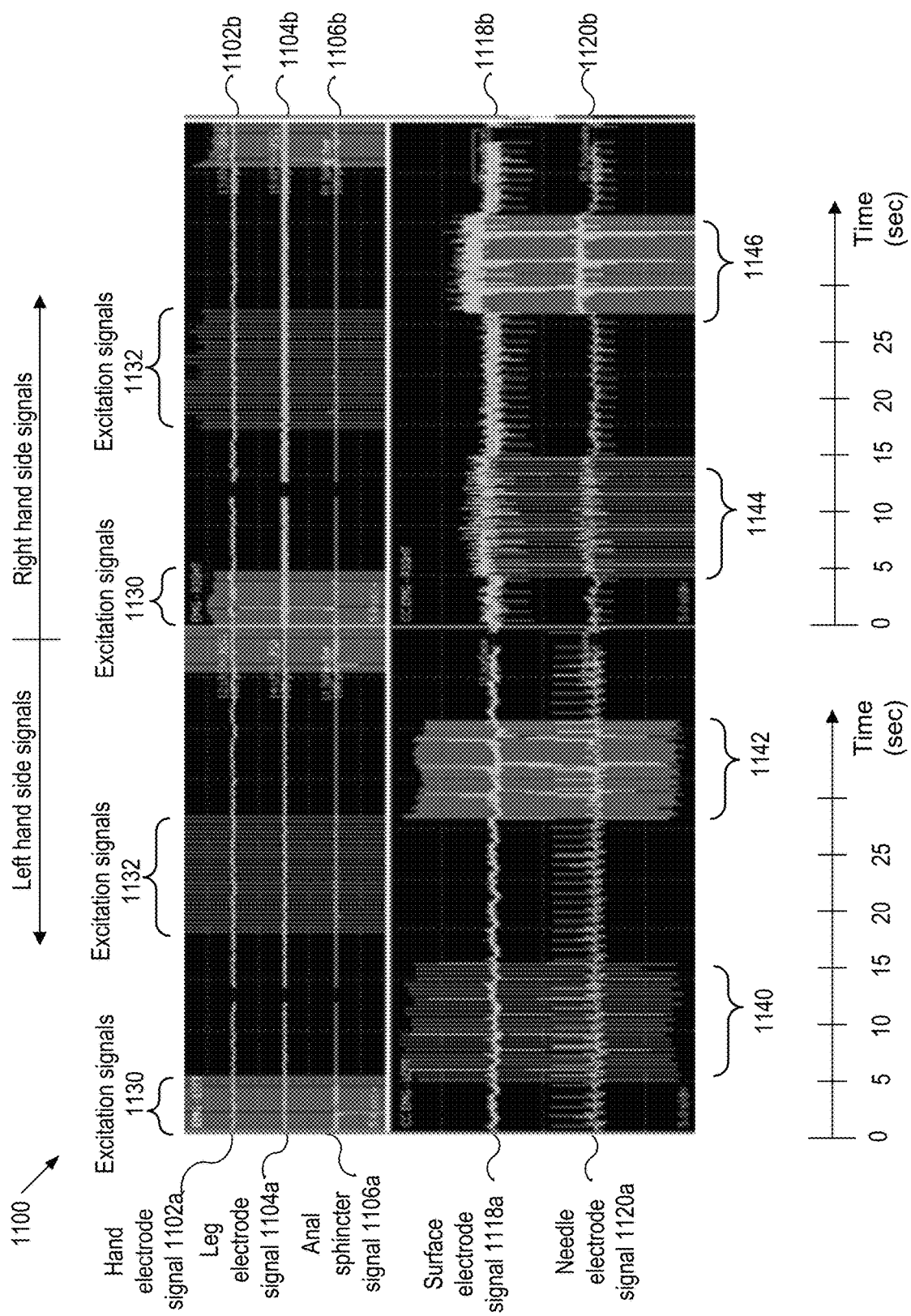

FIG. 11 shows an exemplary screenshot 1100 that includes signals from various electrodes according to embodiments of the present invention. In FIG. 11, the plots 1102*a* (or 1102*b*), 1104*a* (or 1104*b*), 1106*a* (or 1106*b*), 1118*a* (or 1118*b*), and 1120*a* (or 1120*b*) are signals from the pair of surface electrodes 217 on the left (or right) hand, the pair of surface electrodes 219 on the left (or right) foot, the pair of needle electrodes 214 inserted in the left (or right) hand side of the external anal sphincter, the pair of surface electrodes 212 on the left (or right) hand side skin of the penis 209, and the pair of needle electrodes 216 inserted into the left (or right) corpus cavernosum, respectively.

In FIG. 11, two sets of excitation electrical pulses 1130 and 1132 are applied repeatedly in the alternative manner. The first set (train) of electrical pulses 1130 is applied to the tip electrode 422 (or 432) of the laparoscope 420 (or 430) at 5.1 Hz for 10 seconds and the tip electrode 422 (or 432) may be located on the tissue that is likely to contain the right cavernous nerve. The second set (train) of electrical pulses 1132 may be applied to the same tip electrode at 2.0 Hz for 10 seconds at the same location on the tissue. In embodiments, these two trains of electrical pulses 1130 and 1132 may be repeatedly applied in the alternative manner after the prostate is completely removed from the patient's body.

In FIG. 11, for the purpose of illustration, the time axis of the signals 1102, 1104, and 1106 are shifted relative to the time axis of the signals 1118 and 1120. The signals 1140 and 1144 are generated in response to the low frequency excitation signal 1132, while the signals 1142 and 1146 are generated in response to the excitation signal 1130. Also, for the purpose of illustration, only two sets of signals 1140 and 1142 (and 1144 and 1146) are shown on the time axis. However, it should be apparent to those of ordinary skill in the art that the electrodes 212 and 216 repeatedly generate signals that are similar to the signals 1140, 1142, 1144, and 1146 in response to the repeated signals 1130 and 1132.

As shown in the signal portions 1140, 1142, 1144 and 1146, the corpus cavernosum responses to both high and low frequency excitation signals 1130 and 1132. In embodiments, since each of the base signals of the two plots 1118*b* and 1120*b* show sufficiently large peak amplitude and width, the device 210 may determine that the impedance change of the body between the electrodes 212 (or 216) is evident and the right cavernous nerve is not injured during the RP process.

Figure 12:
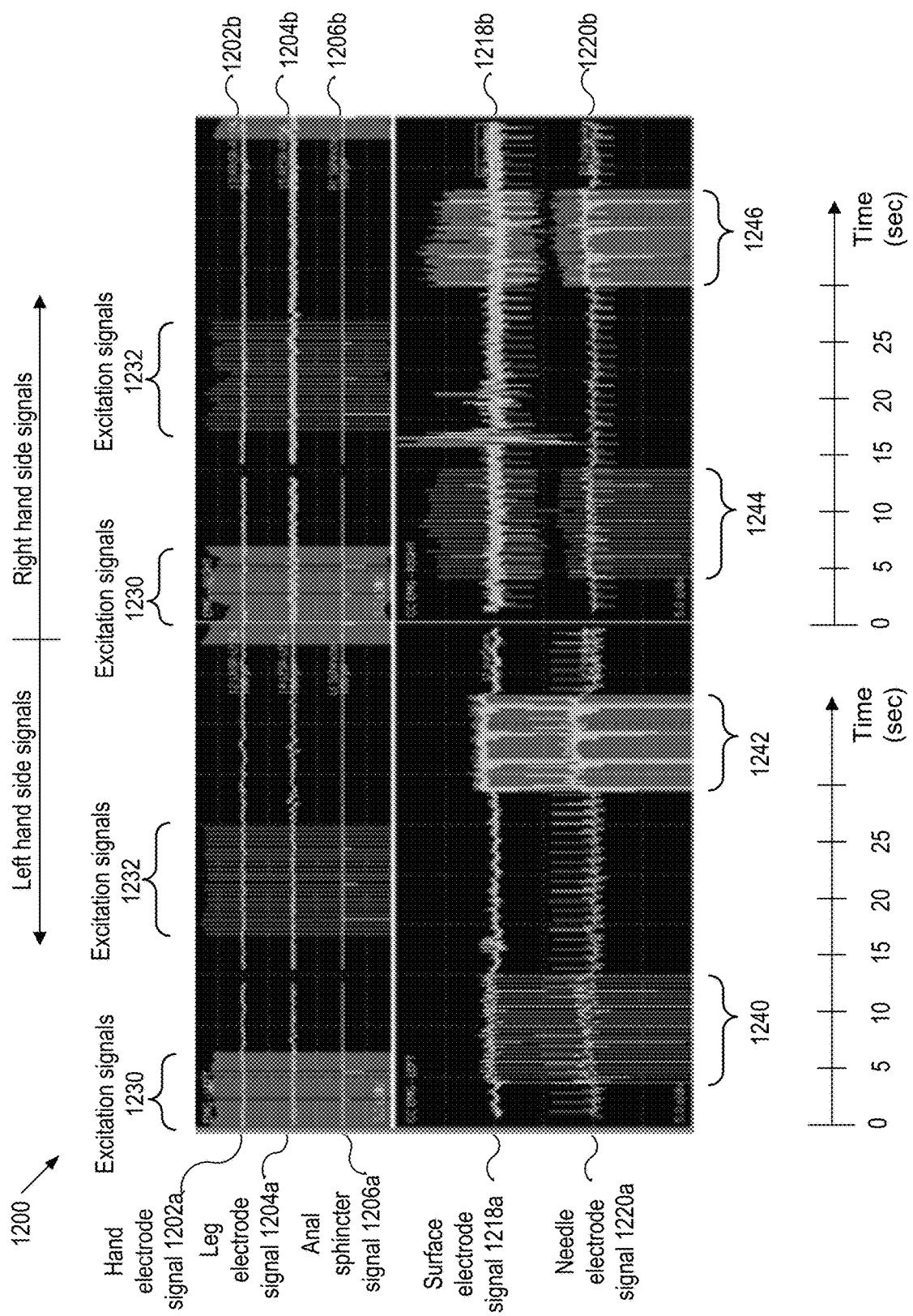

FIG. 12 shows an exemplary screenshot 1200 that includes signals from various electrodes according to embodiments of the present invention. In FIG. 12, the plots 1202*a* (or 1202*b*), 1204*a* (or 1204*b*), 1206*a* (or 1206*b*), 1218*a* (or 1218*b*), and 1220*a* (or 1220*b*) are signals from the pair of surface electrodes 21 on the left (or right) hand, the pair of surface electrodes 219 on the left (or right) foot, the pair of needle electrodes 214 inserted in the left (or right) hand side of the external anal sphincter, the pair of surface electrodes 212 on the left (or right) hand side skin of the penis 209, and the pair of needle electrodes 216 inserted into the left (or right) corpus cavernosum, respectively.

FIG. 12 is similar to FIG. 11, with the difference that the two trains of electrical excitation pulses 1230 (at 5.1 Hz for 10 seconds) and 1232 (2.0 Hz for 10 seconds) are repeatedly and alternatively applied to the tissue that is likely to contain the left cavernous nerve through the tip electrode 422 (or 432) of the laparoscope 420 (or 430). The portions 1240 and 1242 of plots 1218*a* and 1220*a* show the impedance change of the body between the electrodes 212 (and 216) on the left hand side of the penis (and in the left corpus cavernosum). Also, the portions 1244 and 1246 of plots 1218*b* and 1220*b* show the impedance change of the body between the electrodes from the electrodes 212 (and 216) on the right hand side of the penis (and in the right corpus cavernosum).

As shown in FIG. 12, the corpus cavernosum shows larger response at the high frequency excitation signals 1230 than the low frequency excitation signals 1232. In embodiments, since each of the base signals of the two plots 1218*a* and 1220*a* show sufficiently large peak amplitude and width, the device 210 may determine that the impedance change of the body between the electrodes 212 (or 216) is evident and the left cavernous nerve is not injured during the RP process.

It is noted that the electrical excitation signals in FIGS. 11 and 12 may be applied before and during the removal of the prostate from the patient's body. By analyzing the signals similar to those in FIGS. 11 and 12, the device 210 may determine whether the right and left cavernous nerves are damaged during the removal process of the prostate.

Figure 13:
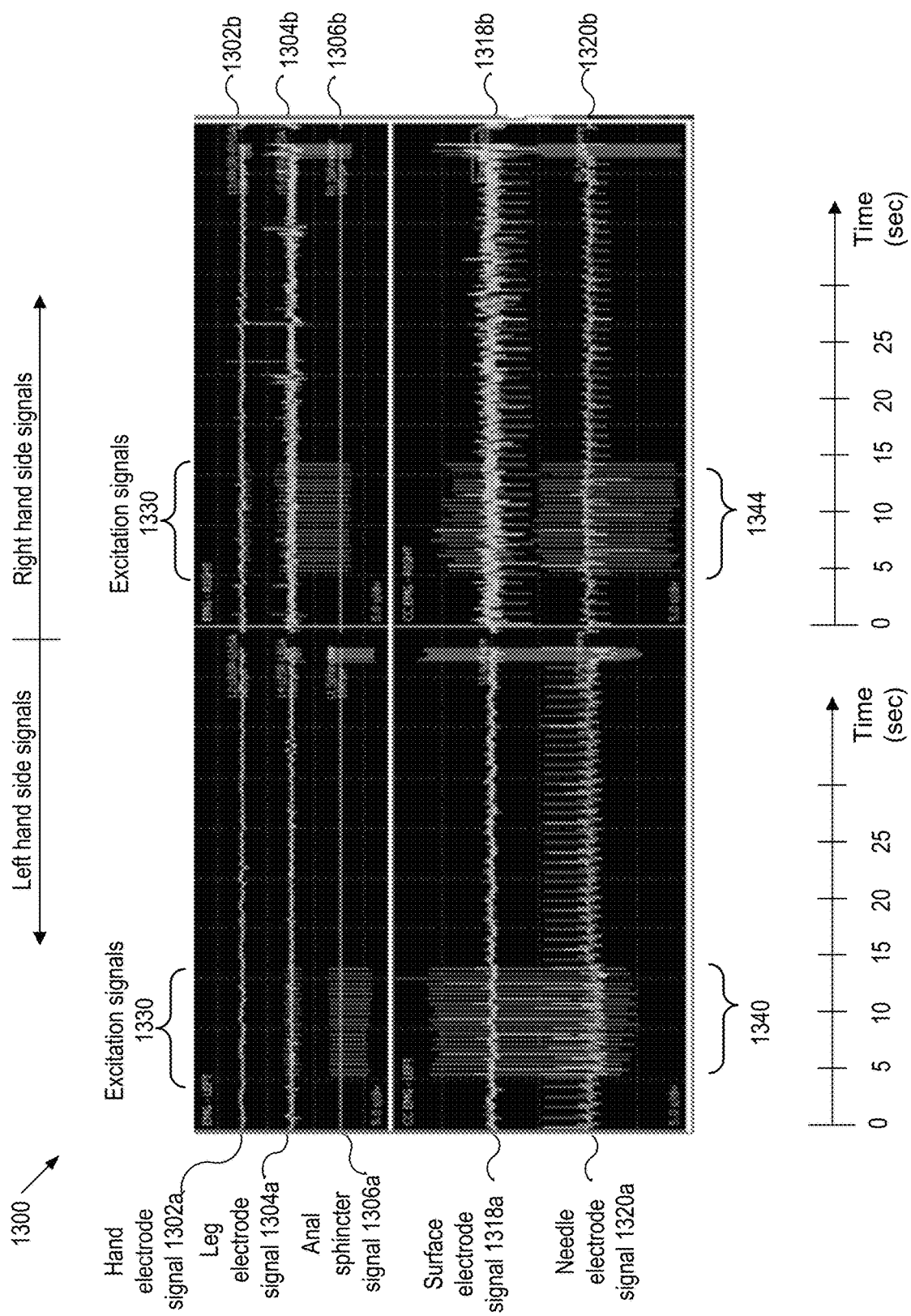

FIG. 13 shows an exemplary screenshot 1300 that includes signals from various electrodes according to embodiments of the present invention. In FIG. 13, the plots 1302*a* (or 1302*b*), 1304*a* (or 1304*b*), 1306*a* (or 1306*b*), 1318*a* (or 1318*b*), and 1320*a* (or 1320*b*) are signals from the pair of surface electrodes 217 on the left (or right) hand, the pair of surface electrodes 219 on the left (or right) foot, the pair of needle electrodes 214 inserted in the left (or right) hand side of the external anal sphincter, the pair of surface electrodes 212 on the left (or right) hand side skin of the penis 209, and the pair of needle electrodes 216 inserted into the left (or right) corpus cavernosum, respectively.

In FIG. 13, a train of electrical excitation pulses 1330 is applied through the tip electrode 422 (or 432) of the laparoscope 420 (or 430) at 2.0 Hz for 10 seconds and the tip may be located on the pelvic inner wall and somewhat remote from the NVB (i.e., the cavernous nerve). As depicted, the plots 1318 and 1320 do not show change in the impedance of the body between the electrodes 212 (or 216), which implies that the cavernous nerve is not located near the point where the tip probe is located.

In embodiments, the train of electrical excitation pulses applied to the tip electrode of the laparoscope 420 (or 430) may have the frequency range of 2.0-50.0 Hz and duration of 10 seconds or more, even though other frequency range and duration may be used to generate the signals in the FIGS. 9-13.

In FIGS. 9-13, the bipolar electrode 422 (or 432) is used to apply the excitation signals to the tissue near the prostate. However, it should be apparent to those of ordinary skill in the art that the electrodes 402 or 412 may be used in place of the electrode 422.

Figure 14:
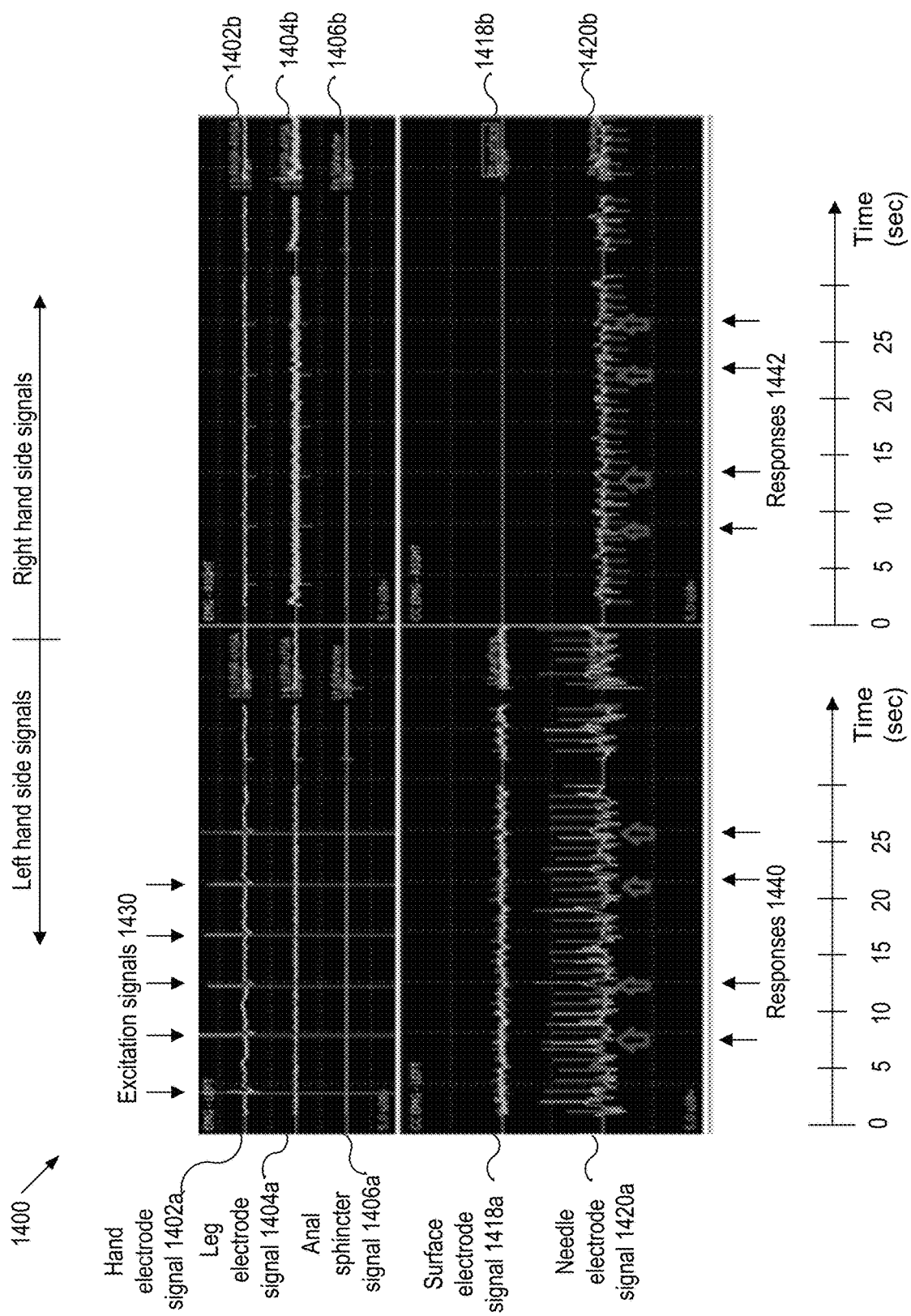
FIG. 14 shows an exemplary screenshot that includes SSR CC-EMG signals according to embodiments of the present invention.

FIG. 14 shows an exemplary screenshot 1400 that includes SSR CC-EMG signals according to embodiments of the present invention. In FIG. 14, electrical excitation signals 1430 are applied through the surface electrode 218 on the left wrist while the plots 1402a (or 1402b), 1404a (or 104b), 1406a (or 1406b), 1418a (or 1418b), and 1420a (or 1420b) are signals from the pair of surface electrodes 217 on the left (or right) hand, the pair of surface electrodes 219 on the left (or right) foot, the pair of needle electrodes 214 inserted in the left (or right) hand side of the external anal sphincter, the pair of surface electrodes 212 on the left (or right) hand side skin of the penis 209, and the pair of needle electrodes 216 inserted into the left (or right) corpus cavernosum, respectively.

The plots in the screenshot 1400 are similar to the plots in the screenshot 800, with the difference that the excitation signals 1430 are applied after the RP process is completed. In FIG. 14, various portions indicated by the arrows 1440 of the plot 1420a show the cavernous electrical activities of left corpus cavernosum in response to the excitation signal 1430 while various portions indicated by the arrows 1432 of the plot 1420b show the cavernous electrical activities of right corpus cavernosum. In embodiments, based on the signals 1420a at the locations indicated by the arrows 1440 and 1420b at the locations indicated by the arrows 1442, the device 210 may determine that the vasomotor function of autonomic nervous system of the corpus cavernosum in response to an excitation signal on the wrist skin is preserved throughout the RP process.

Figure 15:
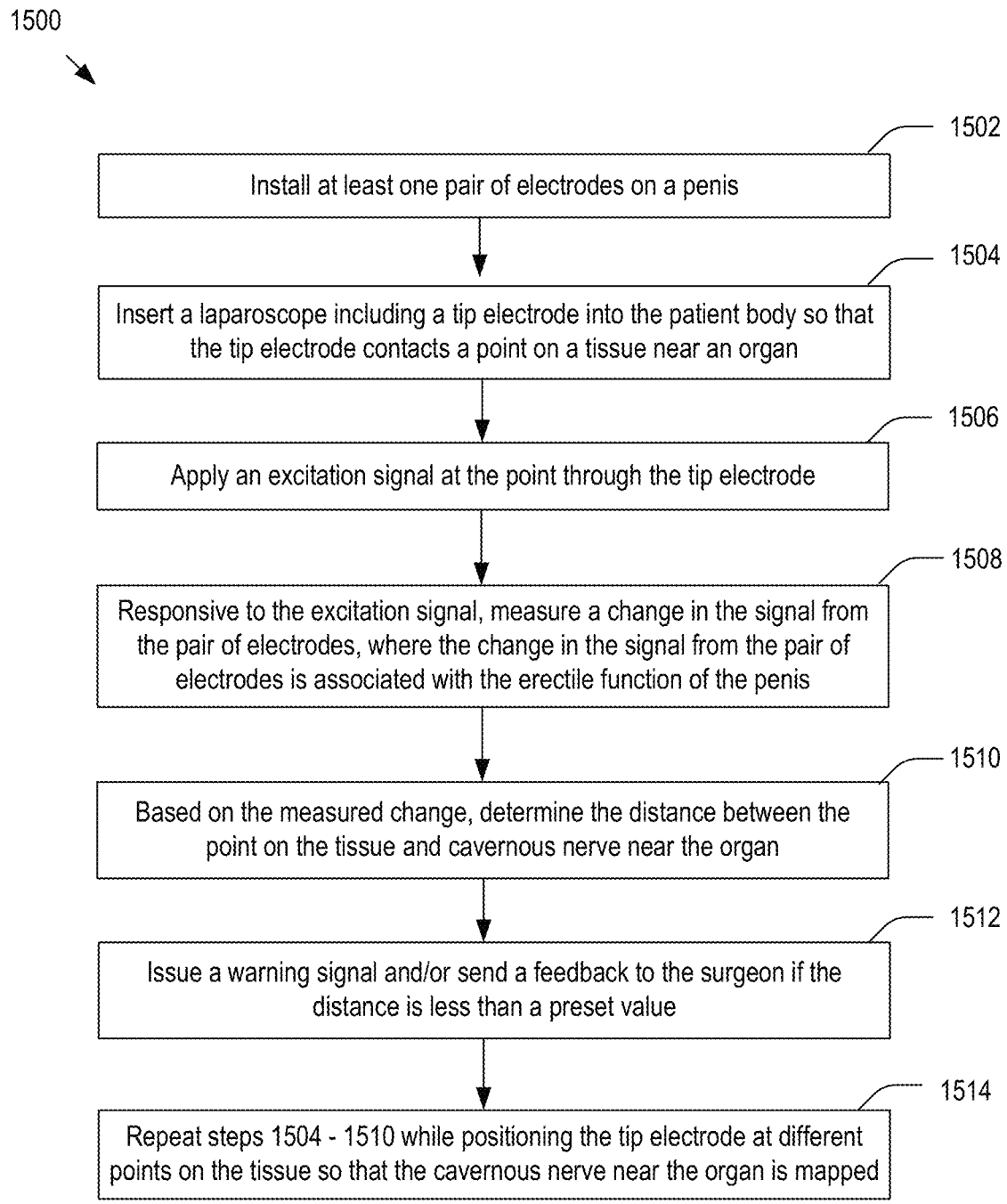
FIG. 15 shows a flowchart of an illustrative process for mapping and preserving cavernous nerves during the RP process according to embodiments of the present invention.

FIG. 15 shows a flowchart of an illustrative process 1500 for mapping and preserving cavernous nerves during the RP process according to embodiments of the present disclosure. At step 1502, at least one pair of electrodes 212 (and/or 216) may be installed on the penis 209. At step 1504, a laparoscope 420 (or 430) including a tip electrode 422 (or 432) may be inserted into the patient body so that the tip electrode contacts a point on the tissue (or NVB) near a target organ, such as prostate, where the cavernous nerve is likely to be in the tissue. In embodiments, the target organ refers to an internal organ on which the surgeon performs a surgical procedure. Then, at step 1506, an excitation signal is applied on the point through the tip electrode. Next, responsive to the excitation signal, the change in the signal from the pair of electrodes 212 (or 216) may be measured, where the change in the signal from the pair of electrodes 212 (or 216) may commensurate with the change in the impedance of the body between electrodes of the pair of electrodes 212 (or 216), i.e. the change is associated with the erectile function of the penis. In embodiments, the excitation signal may include a train of electrical pulses (such as sinusoidal or square waves) that may have the frequency range of 2.0-10.0 Hz and duration of 10 seconds or more.

At step 1510, based on the change in the signal from the pair of electrodes 212 (or 216), the distance between the points on the tissue and the cavernous nerve may be determined. In embodiments, if the magnitude of the peak amplitude of the change in the signal from the pair of electrodes 212 (or 216) exceeds a threshold value, it may be determine that the distance between the portion of the tissue and cavernous nerve is less than a preset value. In alternative embodiments, the minimum threshold to excite the cavernous nerve may be used to determine the distance. The signal generator 304 may repeatedly send the excitation signals to the tip 422 (or 432) while the amplitude of the excitation signal is progressively decreased to the value where the base signal does not show any change. Since the value is the minimum threshold for exciting the cavernous nerve, the device 210 use this threshold to determine the distance between the location of the tip 422 (or 432) and the cavernous nerve 208. In embodiments, the memory 314 may store information of the correlation between the threshold and the distance that is prepared in advance, and the device 210 (more specifically the processor 302) may access the correlation information to determine the distance corresponding to the currently measured minimum threshold.

Optionally, at step 1512, a warning signal may be issued to the surgeon if the tip electrode includes a surgical tool, such as knife, and the distance between the point and cavernous nerve is less than the preset value. At step 1514, the steps 1504-1510 may be repeated while positioning the tip electrode at different points on the tissue so that the cavernous nerve near the target organ is mapped.

In FIGS. 2-15, the systems and methods for mapping, monitoring, and preserving the cavernous nerves are described in conjunction with the RP process. However, it should be apparent to those of ordinary skill in the art that the systems and methods may be applied to any suitable type of surgery in the pelvic region. For instance, during a rectal cancer surgery, the surgeon may damage the cavernous nerve that are located near the rectum, and as such, the systems and methods described in conjunction with FIGS. 2-15 may be used for mapping and monitoring the cavernous nerves near the rectum.

FIGS. 10, 11, 12, and 13 show signals from various sensors in response to an electrical excitation pulse(s) applied through the tip electrode 422 (or 432) of the laparoscope 420 (or 430). However, the electrical excitation pulse(s) may be applied through other types of electrode. For instance, to check if the cavernous nerve is damaged during an open surgery, a surgeon may apply an electrical excitation pulse to the tissue that is likely to contain the cavernous nerve during an open surgery. In such a case, the tip electrode 422 (or 432) may not be necessarily attached to the distal end of a laparoscope, i.e., the laparoscope 420 (or 430) may be replaced by a suitable device that includes the tip electrode 422 (or 432).

In embodiments, one or more computing system may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present invention may be implemented in any instruction-execution/computing device or system capable of processing data, including, without limitation laptop computers, desktop computers, and servers. The present invention may also be implemented into other computing devices and systems. Furthermore, aspects of the present invention may be implemented in a wide variety of ways including software (including firmware), hardware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 16:
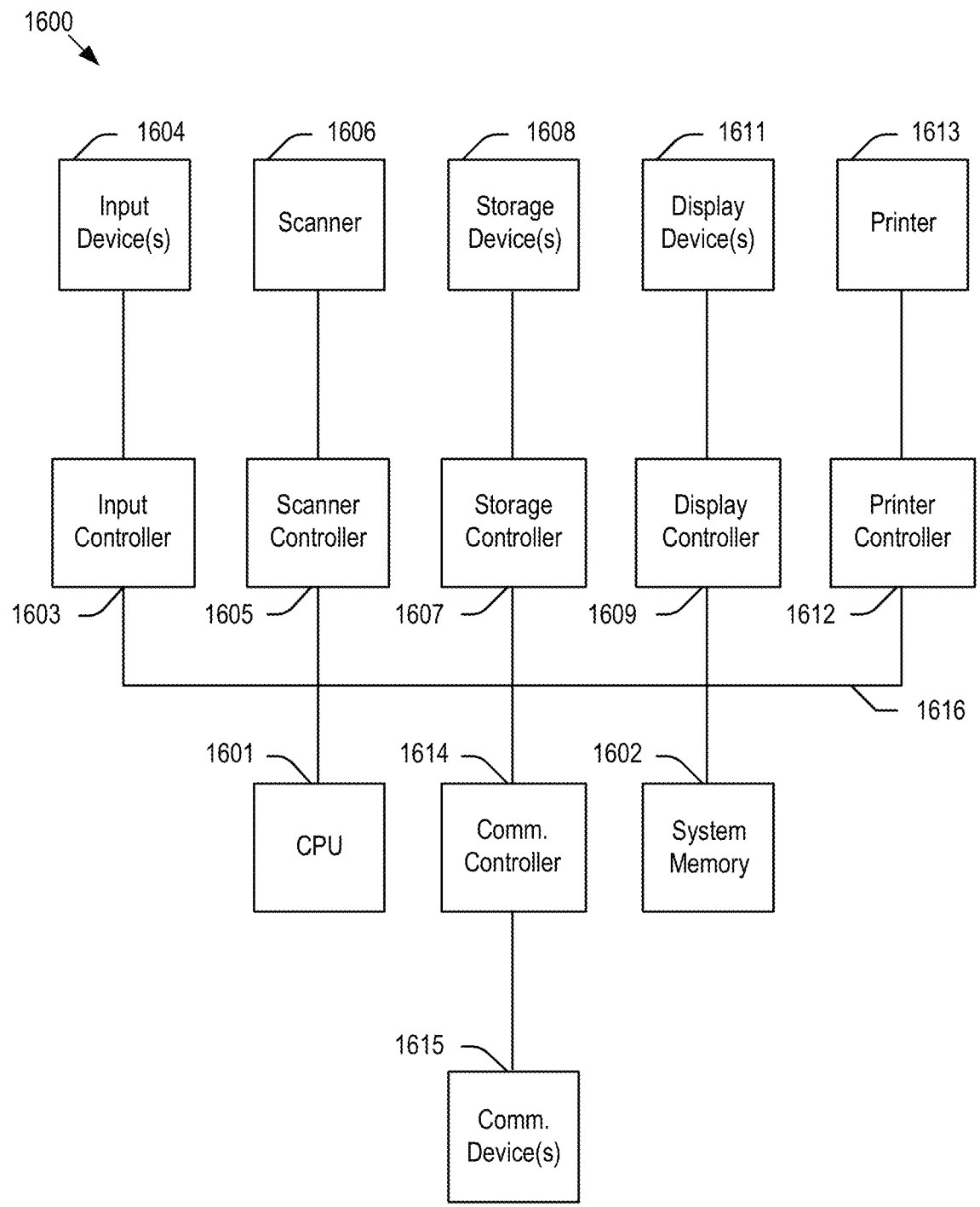
FIG. 16 shows a computer system according to embodiments of the present invention.

Having described the details of the invention, an exemplary system 1600, which may be used to implement one or more aspects of the present invention, will now be described with reference to FIG. 16. The computing system 211 (or the device 210) in FIG. 2 may include one or more components in the system 1600. As illustrated in FIG. 16, system 1600 includes a central processing unit (CPU) 1601 that provides computing resources and controls the computer. CPU 1601 may be implemented with a microprocessor or the like, and may also include a graphics processor and/or a floating point coprocessor for mathematical computations. System 1600 may also include a system memory 1602, which may be in the form of random-access memory (RAM) and read-only memory (ROM).

A number of controllers and peripheral devices may also be provided, as shown in FIG. 16. An input controller 1603 represents an interface to various input device(s) 1604, such as a keyboard, mouse, or stylus. There may also be a scanner controller 1605, which communicates with a scanner 1606. System 1600 may also include a storage controller 1607 for interfacing with one or more storage devices 1608 each of which includes a storage medium such as magnetic tape or disk, or an optical medium that might be used to record programs of instructions for operating systems, utilities and applications which may include embodiments of programs that implement various aspects of the present invention. Storage device(s) 1608 may also be used to store processed data or data to be processed in accordance with the invention. System 1600 may also include a display controller 1609 for providing an interface to a display device 1611, which may be a cathode ray tube (CRT), a thin film transistor (TFT) display, or other type of display. System 1600 may also include a printer controller 1612 for communicating with a printer 1613. A communications controller 1614 may interface with one or more communication devices 1615, which enables system 1600 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 1616, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present invention may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

What is claimed is:

1. A system for mapping a cavernous nerve near a prostate, comprising:
one or more processors; and
a memory that is communicatively coupled to the one or more processors and stores one or more sequences of instructions, which when executed by one or more processors causes steps to be performed comprising:
(a) applying an excitation signal to an electrode that is configured to directly contact a portion of a periprostatic neurovascular tissue surrounding a prostate, the excitation signal being configured to stimulate a cavernous nerve embedded in the periprostatic neurovascular tissue;
(b) responsive to the excitation signal, measuring a change in a signal from a pair of electrodes configured to be installed on a penis, the change in the signal being associated with an amount of blood pooled into the penis due to an erectile function of the penis; and
(c) based on the change in the signal from the pair of electrodes, determining a distance between the portion of the periprostatic neurovascular tissue and the cavernous nerve.

2. The system of claim 1, wherein the pair of electrodes includes a pair of surface electrodes configured to be attached to a surface of the penis.

3. The system of claim 1, wherein the pair of electrodes includes a pair of needle electrodes configured to be inserted into a corpus cavernosum of the penis.

4. The system of claim 1, wherein the step (c) includes:
measuring a peak amplitude of the change in the signal from the pair of electrodes; and
if the peak amplitude exceeds a threshold, determining that the distance is within a preset range.

5. The system of claim 4, further comprising a speaker,
wherein the memory further stores one or more sequences of instructions, when executed by the one or more processors, causes steps to be performed comprising:
causing the speaker to issue a warning signal when the distance is within the preset range.

6. The system of claim 4, further comprising a display,
wherein the memory further stores one or more sequences of instructions, when executed by the one or more processors, causes steps to be performed comprising:
causing the display to display a warning signal when the distance is within the preset range.

7. The system of claim 1, wherein the electrode is located at a tip of a laparoscope and includes a two-prong bipolar electrode or a concentric bipolar electrode.

8. The system of claim 1, wherein the excitation signal includes a train of pulses that have a frequency range of 2-10 Hz and a duration of 10 seconds or more.

9. The system of claim 1, wherein the memory further stores one or more sequences of instructions, when executed by the one or more processors, causes steps to be performed comprising:
repeating the steps (a)-(c) while positioning the electrode at different locations on the periprostatic neurovascular tissue, to thereby map the cavernous nerve.

10. The system of claim 1, further comprising:
a robotic surgery system electrically coupled to the system,
wherein the electrode is located at a tip of a laparoscope and the laparoscope is operated by the robotic surgery system.

11. The system of claim 1, wherein the step (c) includes:
repeating the steps (a)-(b) while an amplitude of the excitation signal is progressively decreased to a value where the sensor signal measured in the step (b) has no change; and
based on the value, determining the distance between the portion of the periprostatic neurovascular tissue and the cavernous nerve.

12. A method for mapping a cavernous nerve near a prostate, comprising:
(a) applying an excitation signal to an electrode that is configured to directly contact a portion of a periprostatic neurovascular tissue surrounding a prostate, the excitation signal being configured to stimulate a cavernous nerve embedded in the periprostatic neurovascular tissue;
(b) responsive to the excitation signal, measuring a change in a signal from a pair of electrodes configured to be installed on a penis, the change in the signal being associated with an amount of blood pooled into the penis due to an erectile function of the penis; and
(c) based on the change in the signal from the pair of electrodes, determining a distance between the portion of the periprostatic neurovascular tissue and the cavernous nerve.

13. The method of claim 12, wherein the pair of electrodes includes a pair of surface electrodes configured to be attached to a surface of the penis.

14. The method of claim 12, wherein the pair of electrodes includes a pair of needle electrodes configured to be inserted into a corpus cavernosum of the penis.

15. The method of claim 12, wherein the step (c) includes:
measuring a peak amplitude of the change in the signal from the pair of electrodes; and
if the peak amplitude exceeds a threshold, determining that the distance is within a preset range.

16. The method of claim 15, further comprising:
issuing a warning signal when the distance is within the preset range.

17. The method of claim 12, further comprising:
repeating the steps (a)-(c) while positioning the electrode at different locations on the periprostatic neurovascular tissue, to thereby map the cavernous nerve.

18. The method of claim 12, wherein the step (c) includes:
repeating the steps (a)-(b) while an amplitude of the excitation signal is progressively decreased to a value where the signal measured in the step (b) has no change; and
based on the value, determining the distance between the portion of the periprostatic neurovascular tissue and the cavernous nerve.

19. A non-transitory computer-readable medium or media comprising one or more sequences of instructions which, when executed by one or more processors, causes steps to be performed comprising
(a) applying an excitation signal to an electrode that is configured to directly contact a portion of a periprostatic neurovascular tissue surrounding a prostate, the excitation signal being configured to stimulate a cavernous nerve embedded in the periprostatic neurovascular tissue;

(b) responsive to the excitation signal, measuring a change in a signal from a pair of electrodes configured to be installed on a penis, the change in the signal being associated with an amount of blood pooled into the penis due to an erectile function of the penis; and (c) based on the change in the signal from the pair of electrodes, determining a distance between the portion of the periprostatic neurovascular tissue and the cavernous nerve.

20. The non-transitory computer-readable medium or media of claim 19, wherein the step (c) includes:

repeating the steps (a)-(b) while an amplitude of the excitation signal is progressively decreased to a value where the signal measured in the step (b) has no change; and based on the value, determining the distance between the portion of the periprostatic neurovascular tissue and the cavernous nerve.

* * * * *